United States Patent
Williams et al.

[11] Patent Number: 5,918,261
[45] Date of Patent: Jun. 29, 1999

[54] MULTI-ELECTRODE GAS SENSORS AND METHODS OF MAKING AND USING THEM

[75] Inventors: David Edward Williams, Abingdon; Pratt Keith Francis Edwin, Tamworth, both of United Kingdom

[73] Assignee: Capteur Sensors & Analysers, Ltd., Didcot, United Kingdom

[21] Appl. No.: 08/894,465

[22] PCT Filed: Dec. 23, 1996

[86] PCT No.: PCT/GB96/03220

§ 371 Date: Aug. 20, 1997

§ 102(e) Date: Aug. 20, 1997

[87] PCT Pub. No.: WO97/23777

PCT Pub. Date: Jul. 3, 1997

[30] Foreign Application Priority Data

Dec. 22, 1995 [GB] United Kingdom .................. 9526393

[51] Int. Cl.$^6$ ...................................................... G01N 27/12
[52] U.S. Cl. ............................................. 73/31.06; 338/34
[58] Field of Search ................................ 73/31.06, 23.31; 338/34, 308; 422/90

Primary Examiner—Michael Brock
Attorney, Agent, or Firm—Woodcock Washburn Kurtz Mackiewicz & Norris, LLP

[57] ABSTRACT

A resistive gas sensor has a gas sensing layer (11) overlaid as a layer on an array of electrodes (12, 14, 16) with unequal gaps (22, 24) between them. Signals from the different electrodes represent resistances in different regions of the sensing layer. The layer is applied as a succession of sub-layers, with application of each sub-layer modifying the microstructure of the preceding sub-layers. The resulting variation in microstructure within the sensing layer (11) is used for distinguishing between a reactive gas and a less reactive gas. The sensor has domestic applications for carbon monoxide detection.

14 Claims, 6 Drawing Sheets

MULTI-ELECTRODE GAS SENSORS AND METHODS OF MAKING AND USING THEM

This invention relates to resistive gas sensors (also referred to as gas-sensitive resistors, or sensing devices), of the multi-electrode kind, i.e. a resistive gas sensor having three or more electrodes for receiving signals from different regions of a gas sensing element of the device. The invention also relates to methods of making such sensors, and to methods of detecting a target gas using a multi-electrode resistive gas sensor.

Such sensors will also be referred to herein as multi-electrode array devices.

Multi-electrode resistive gas sensors are disclosed in, for example, the document W092/21018, which teaches operating principles of multi-electrode gas-sensitive resistors which are self-diagnostic. These principles are developed further in the document W095/04927. Reference is invited to those documents for more information; and to the papers by D. E. Williams and K. F. E. Pratt, in J. Chem. Soc. Faraday Trans., 1995, 91, 1961 (referred to herein, for convenience, as "Williams I"), which presents the theoretical basis for the operation of the sensors, and in J. Chem. Soc. Faraday Trans., 1995, 91, 3307 (referred to herein, for convenience, as "Williams II"), which describes the experimental demonstration of the ability of such devices to detect poisoning of their own surfaces.

The gas sensing element consists generally of a porous body (typically a thin layer) of an oxide, which is to be understood to include combinations (such as a mixture) of more than one oxide, with or without additives for various purposes. Such optional additives may include catalytic material, for example to promote combustion of a particular gas in the mixture to which the sensor is exposed.

One of the objects of this invention is to provide a resistive gas sensor capable of distinguishing between two gases (e.g. a reactive gas and a less reactive gas) in a gaseous mixture. One example of a reactive gas, in this context, is ethanol, and one example of a less reactive gas is carbon monoxide.

A further object of the invention is to provide a sensor which makes an optimal distinction between a real hazard, such as CO, and a false alarm caused by, for example, ethanol.

According to the invention in a first aspect, a resistive gas sensor including: a porous gas sensing element comprising an oxide as active gas-sensitive material, the sensing element having a working surface for contact with an atmosphere; and at least three electrodes in electrical contact with the sensing element, for receiving signals from different regions of the latter, is characterised in that the microstructure of the sensing element is graded as between different regions of the sensing element.

Preferably, the said microstructure is finer in the basal region than in regions of the element closer to its working surface.

The sensing element is typically in the form of a layer, which preferably comprises a plurality of sub-layers, overlaid one on another, with each sub-layer having a different microstructure from the other sub-layer or sub-layers.

In preferred embodiments of the invention the electrodes comprise a first electrode, a common second electrode defining a narrow gap between the first and second electrodes, and a third electrode defining a wide gap between the second and third electrodes, whereby output signals from the first electrode represent electrical resistance in a basal region of the sensing element close to the electrodes, and output signals from the third electrode represent resistance across the whole thickness of the sensing element defined between the electrodes and the working surface.

Preferably, the active sensing material is chromium titanium oxide, with an impurity content comprising $Cr_2O_3$ in the inclusive range 0–30 mol % and/or $TiO_2$.

It will be understood from this that such impurities may be entirely absent, though these and other impurities can be present, as is discussed later herein.

In some embodiments the sensing element includes up to 30% by weight of catalytically active material.

According to the invention in a second aspect, in a method of making a sensor according to the invention, the sensing element is applied as a layer over the electrodes, and in that the said layer is applied in successive stages, each said stage comprising:

screen printing a sub-layer over the electrodes or a selected surface area of the electrodes, or over the last preceding sub-layer as the case may be; and drying the sub-layer, whereby the application of each sub-layer other than the first tends to modify the microstructure of the sub-layer or sub-layers previously applied.

According to the invention in a third aspect, in a method of detecting a target gas in a mixture of gases, using a resistive gas sensor having at least three electrodes to produce electrical resistance signals, the method including processing said signals to obtain information about the target gas and/or the mixture, the sensor is a sensor according to the invention.

In this method, where the mixture includes a reactive first gas and a less reactive second gas, the sensor used has a sensing element the active sensing material of which displays a concentration gradient across the sensing element in response to the first gas, but substantially none in response to the second gas. Sensors according to the invention are especially useful in this context, for distinguishing one gas from the other by the respective presence and absence of a concentration gradient.

A particular example of a practical application of this method is for sensing carbon monoxide, whereby the sensor can distinguish the target gas CO from less reactive gases, such as ethanol, the presence of which could otherwise cause false alarms to be given. An example of the use of the sensors of the invention for such a purpose is in domestic premises.

One preferred sensing material for sensors for use in the methods of the invention is chromium titanate (chromium titanium oxide), in particular $Cr_{2-x}Ti_xO_{3+y}$, where $0.45 \geq x \geq 0.1$ and y is a variable dependent on temperature and oxygen partial pressure, as discussed in the document W095/00836, to which reference is invited for more detail. Chromium titanate is known per se as a material for gas-sensitive resistors; it is a preferred material for some purposes, particularly when prepared as a single-phase material with x=0.2 and operated at temperatures in the range 300–500° C. The Applicants have however been surprised to find in this connection that the exact composition is not critical for manufacture of functional gas-sensitive resistors, although, for optional performance, both purity (chemical and phase purity) and microstructure must be carefully controlled.

As regards impurities, the Applicants have found that functional sensors can be prepared having a very wide range of elements present as impurities, up to 1 atom %. Examples include Na, K, Ca, Mg, Pb, Cd, Bi, Si, Fe, Co, Ni, Ag, S and other alkaline, alkaline earth and transition metals, semimetals and non-metals, Pt, Pd, Ir, Rh, Au and other precious metals. Such elements may indeed be added deliberately (as is known in the art), variously, in order (a) to improve adhesion to substrate and electrodes, (b) to control sintering in the oxide layer, (c) to promote cohesion of the oxide, and/or (d) to modify the concentration profile of the target gas or its decomposition products.

We have also found that phase-purity is not essential for satisfactory performance: unreacted $Cr_2O_3$ present at up to 30 mol % does not prevent the material being functional. Moreover, we have found with some surprise that amounts of $TiO_2$ present beyond the single phase boundary limit of $x \approx 0.45$ do not prevent the material being functional.

We have found that the admixture of catalytically active materials such as Pt or Pd, either decorating the surface of the gas sensing material, or admixed into the gas sensing material, supported on an insulator such as $Al_2O_3$ and co-printed with the gas sensing material, cause useful variations in the response of the resulting device. Up to at least 30% by weight of the catalytically active material may be admixed with the gas sensing material. The catalytically active material may then typically consist of alumina powder platinised with 5% by weight of platinum.

The above mentioned variations arise because the catalytically active material causes a decomposition or transformation of the target gas, resulting in a concentration gradient of the target gas and its transformation products within the porous sensor structure. Such a concentration gradient can be detected and used for distinguishing different target gases, and for self-validating multi-electrode sensors, for example those described in the document WO92/21018.

In particular, $Cr_{2-x}Ti_xO_{3+y}$, whether or not treated with catalytically active metals, is an excellent gas sensing material both for carbon monoxide in air and for ammonia in air. Surprisingly, we have found that, contrary to current thinking, chromium titanate untreated with a catalytically active metal does not catalyse the combustion of either of these gases, or at least not to any significant extent, in the temperature range at which it may be operated as a gas sensor. Consequently, a concentration gradient of these gases is not established within the porous sensor structure.

However, a concentration gradient of solvents such as acetone, ethanol and methanol, which are common interferents to the target gases in circumstances encountered in practice, is indeed established. Hence a multiple-electrode sensing device of $Cr_{2-x}Ti_xO_{3+y}$ can particularly easily distinguish between the real threat from a target gas (such as CO or $NH_3$) and an interference by traces of solvent vapours. It is therefore particularly advantageous to use such devices of this material, whether or not it contains a catalyst.

In a sensing device with multiple-electrodes, the response is determined by a parameter $K_T = kh^2/D$, where k is the pseudo first order rate constant for decomposition of the gas within the porous sensor structure, h is the layer thickness, and D is the diffusivity of the gas through the porous sensor body.

The parameter $K_T$ depends on the temperature and the microstructure of the sensor. This dependence on microstructure arises through the variations of D and k with particle size and packing density. The diffusivity D depends on the porosity, constrictivity and tortuosity of the porous structure. Porosity here means the fraction of the layer volume which is occupied by gas; while constrictivity is a measure of the cross-sectional area of the gas paths through the porous solid; and tortuosity is a measure of their length.

Because the decomposition reaction may be catalysed on the surface of the sensor material (at the gas-solid interface within the pores of the device), the rate constant k depends on its internal surface area. Furthermore, the sensitivity of the device might, in principle, be altered by altering the microstructure. This principle is in fact well known per se for conventional gas sensors of the simple type having only one pair of electrodes, because the effect of the gas on the electrical conductivity of the solid is known to be exerted at the gas-solid interface. It is generally considered in this connection that the consequent modification of conductivity is confined to a zone of some restricted depth below the surface. Consequently, it is considered that the effect of the gas might be greatest at the contacts between particles, that it might depend on whether these contacts were confined to narrow points or were in the form of "necks" between grains, and that it ought to depend on the grain size and whether the grains were agglomerated into larger lumps.

In consequence of the known effects of microstructure on sensitivity, other work in the field is strongly directed towards manufacture of devices with ever smaller particle size, and with controlled but very small particle size.

It might be thought self-evident that devices with the smallest particle size consistent with stability of the microstructure at the operating temperature should be the most sensitive, and therefore the most desirable. However, in the multiple-electrode sensing devices of the invention, their actual sensitivity pattern is not predictable in this way, because a change in the microstructure not only alters sensitivity, but also alters the parameter $K_T$ that controls the relationship between the different outputs of the device, in ways which are neither intuitively obvious nor evident from the prior art, even to the person skilled in the art, because of the multiplicity of factors involved.

The invention provides a very simple means whereby the surprising result is obtained that subtle alterations in microstructure can be made which have beneficial effects on the discrimination between gases that can be achieved with multi-electrode array devices. In particular, the invention permits optimisation of the discrimination between the signal due to a less reactive gas such as carbon monoxide and that due to a more reactive gas, such as ethanol or other common solvents. This optimisation relies on achieving a microstructure and operating temperature at which:

(1) the ratio $K_T$ for the more reactive gas (e.g. ethanol) is greater than unity, so that a concentration gradient is established for that gas within the device; this is not difficult because vapours such as ethanol are easily combusted on the surface of the device, even with a coarse, open microstructure such as may be achieved by inducing agglomeration of particles during the synthesis of the sensor material;

(2) with the same microstructure and operating temperature, $K_T$ for the less reactive gas (e.g. carbon monoxide) is substantially less than unity, so that there is no concentration gradient of carbon monoxide through the layer; and (3) the microstructure is graded, in such a way that the sensitivity to all gases is greater in the inner part of the layer than in the outer layer. This is achieved in general by providing a finer microstructure in the inner part of the layer, i.e. the basal region of the sensing element, distal from the working surface of the latter exposed to the gas, and proximal to the electrodes.

The resulting multiple-electrode sensor has excellent sensitivity for carbon monoxide and excellent discrimination between real alarms due to carbon monoxide, and false alarms due to the presence of solvent vapours or ethanol.

Some embodiments of the invention will now be described and discussed, by way of example only and, where appropriate, with reference to the accompanying drawings, in which.

Figure 1:
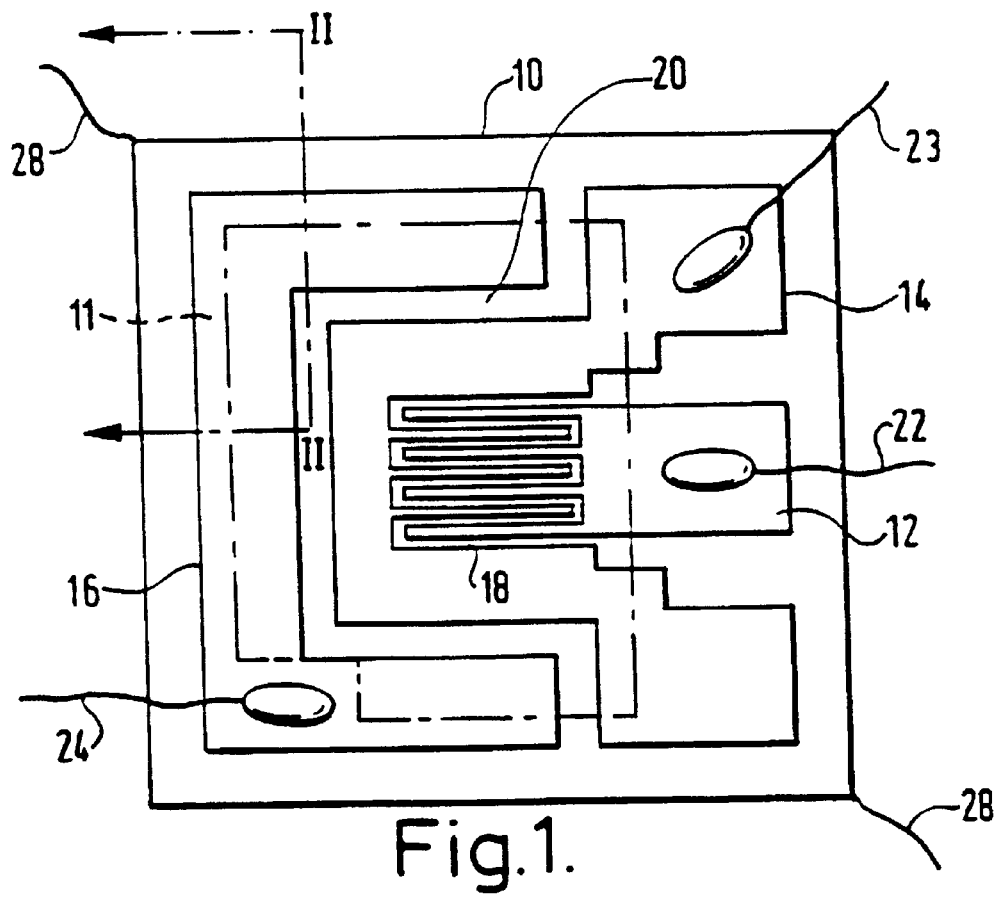
FIG. 1 shows an electrode layout for a gas sensor of the multiple-electrothe multiple-electrode type having two electrode gaps.
Figure 2:
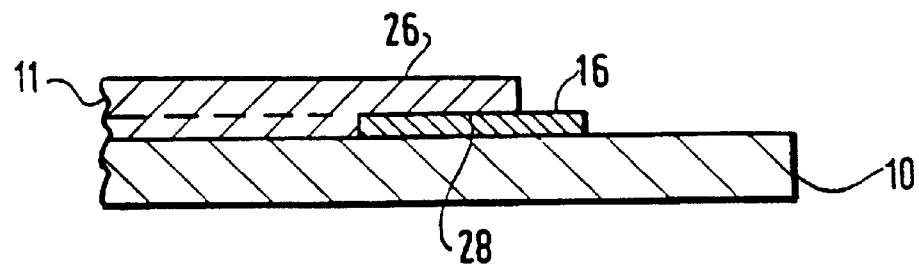
FIG. 2 is an enlarged scrap view (not to scale), in cross section on the line II—II in FIG. 1.

FIGS. 1 and 2 show a typical layout for a multi-electrode sensor, comprising a flat substrate 10 (about 2 mm square, for example), having a front or sensing side seen in FIG. 1, and a back side. Three electrodes 12, 14, 16 are carried on the front side of the substrate, and an oxide sensing layer 11 (or sensing element) is overlaid on the electrodes, in electrical contact with the latter through a base surface 28 of the element 11. In FIG. 1, the sensing layer is omitted, so as to show the electrodes, but its outline is indicated at 11 in phantom lines.

The outer or working surface 26 of the sensing element 11 is exposed, in use, to an atmosphere containing a target gas or gases to be sensed (which term is to be interpreted broadly, to include detection and measurement with a view to the monitoring, identification, and/or analysis, as defined, of the target gas or gases). A "narrow" gap 18, of 20 μm in this example, is defined between the inner electrode 12 and the middle or common electrode 14, which here have an interleaved, comb-like configuration. A "wide" gap 20, i.e. a gap wider than the narrow gap 18, and being of 100 μm in this example, is defined between the middle electrode 14 and the outer electrode 16. Electric leads 22, 23, 24 are spot welded to the electrodes 12, 14, 16 respectively, so that a signal corresponding to the resistance $R_N$ across the narrow gap 22 can be taken from the sensor via the leads 22 and 23, and a signal corresponding to the resistance $R_w$ across the wide gap 20 can be taken via the leads 23 and 24.

Further leads 28 are connected to a heater (not visible) on the back of the substrate 10.

Figure 3:
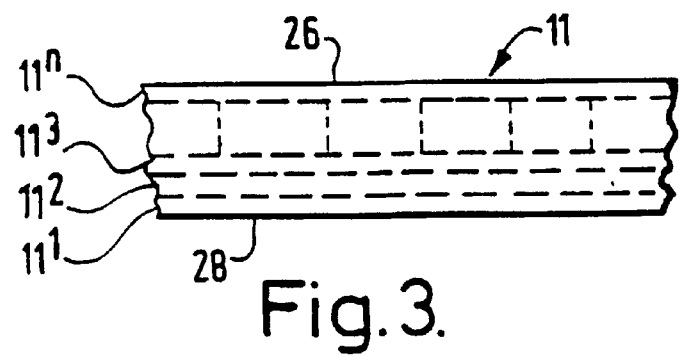
FIG. 3 shows the configuration of the sensing layer as a set of sub-layers.

With reference to FIG. 3, the oxide sensing element here consists of a layer which can be considered as comprising a number of sub-layers $11^1$, $112^2$, $11^3$... $11^n$. The boundary regions between these sub-layers, where one sub-layer merges into the next, are indicated by broken lines in FIG. 3. The sub-layer $11^1$ is adjacent to the electrodes; the region consisting of the sub-layer $11_1$ and (to a decreasing extent going away from the latter) adjacent sub-layers can be regarded as a "basal" region of the element 11.

The arrangement whereby the narrow gap 22 in FIG. 1 is defined by an interdigitated pattern of narrow strips, forming part of the electrodes 12 and 14, tends to cause the electric current to flow only through the basal region of the sensing element. The outer, or wide, electrode 16 not only defines the wide gap 20, but is also not interdigitated. Instead, the electrode 16 is in the form of wide strips: this arrangement tends to cause the electric current to flow uniformly through the whole thickness of the sensing layer 11.

EXAMPLE 1

A mixed powder of chromium trioxide and titanium dioxide is prepared by weighing commercially available powders (such as those available from Aldrich Chemical Company) in the ratio 0.9 mole $Cr_2O_3$: 0.2 mole $TiO_2$, and placing these powders into a cylindrical vessel, together with milling media (zirconia, alumina and steatite have all proved satisfactory) and sufficient solvent (water, acetone, ethanol, isopropyl alcohol and methyl ethyl ketone have all proved satisfactory) to make a highly fluid mixture. This mixture is then ball-milled for sufficient time to achieve an intimate mixture of the oxide powders.

Following this step, the milling media are filtered from the suspension, the solvent is evaporated and the resultant dry powder is fired for 1000° C. for 1 to 16 hours. Shorter firing times, or lower firing temperatures, are found to result in some unreacted chromium trioxide and titanium dioxide being present. Where this is the case, the performance of the resulting devices is not the best achievable, but functionality is generally unimpaired.

The fired powder is mixed in a triple-roll mill with a conventional formulation of solvent and polymer for preparation into an ink suitable for screen-printing. This is then screen-printed on to alumina substrates carrying, on the front or sensing side, an array of electrodes, which may for example be generally as shown in FIG. 1. On the back side, the substrate has a platinum resistance track used both to heat the sensing element and to maintain it at constant temperature. The ratio of powder to polymer in the screen-printing ink is adjusted to give an open porosity of some 30–60% in the final sensing element. The finished sensor is typically as already described with reference to FIGS. 1 to 3.

The sensor layer is deposited over the electrodes in a succession of printing steps with intermediate drying. Each step lays down a layer having a dried thickness of 10 μm. The intermediate drying is carried out under an infra-red lamp, or in an oven at approximately 110° C. A total layer of thickness 90 μm is deposited in this way, in a succession of nine printing and drying steps.

The Williams I paper mentioned earlier herein showed that the important fabrication parameters were the ratios a/h and b/h, where a is half the width of the inter-electrode gap, b is half the electrode width, and h is the oxide layer thickness. In the example shown in FIG. 1, for the narrow gap 18, a/h=b/h≅0.1, while for the wide gap 20, a/h≅0.8 and b/h is very large.

Microscopy has shown that, with material fabricated in this way, the final device, viewed from on top, had a very open microstructure in which the basic crystallite size was 0.1–1 μm, and in which there were both large agglomerates (up to 10 μm) and large open pores (1–10 μm). Table 1, below, shows the results of exposure of this device to propan-2-ol and to carbon monoxide at low concentrations in air. The resistance rose markedly on both electrodes in both gases, which illustrates the problem of interference between the desired signal (i.e. the response to carbon monoxide) and false alarm signals (i.e. the response to solvents and alcohol vapour).

However, Table 1 also shows that the variation of the resistance ratio, $T_W/T_N$, discriminated between the two gases. For propan-2-ol, the ratio increased when the gas was present, as may be expected from the Williams I and W092/21018 documents. This means that propan-2-ol showed a concentration gradient through the layer, having a much lower concentration in the basal region of the layer probed by the narrow gap. Consequently the resistance response for the narrow gap was smaller and the ratio $R_W/R_N$ increased. In contrast, for carbon monoxide, $R_W/R_N$ was most unexpectedly found to decrease.

TABLE 1

Behaviour of sensors prepared according to Example 1

|  | Air | Propan-2-ol (200 ppm) | Carbon monoxide (400 ppm) |
|---|---|---|---|
| Sensor resistance at 390° C.: |  |  |  |
| wide gap | 684kΩ | 5.23MΩ | 1.76MΩ |
| narrow gap | 180kΩ | 850kΩ | 627kΩ |
| Sensor response Rgas/Rair: |  |  |  |
| wide gap |  | 7.64 | 2.57 |
| narrow gap |  | 4.72 | 3.48 |
| Resistance ratio $R_W/R_N$ | 3.80 | 6.15 | 2.81 |

This means that carbon monoxide can be distinguished from propan-2-ol by simple inspection of the ratio and its change. Similar results have been obtained with ethanol, ethyl acetate and other common solvent vapours.

Figure 4:
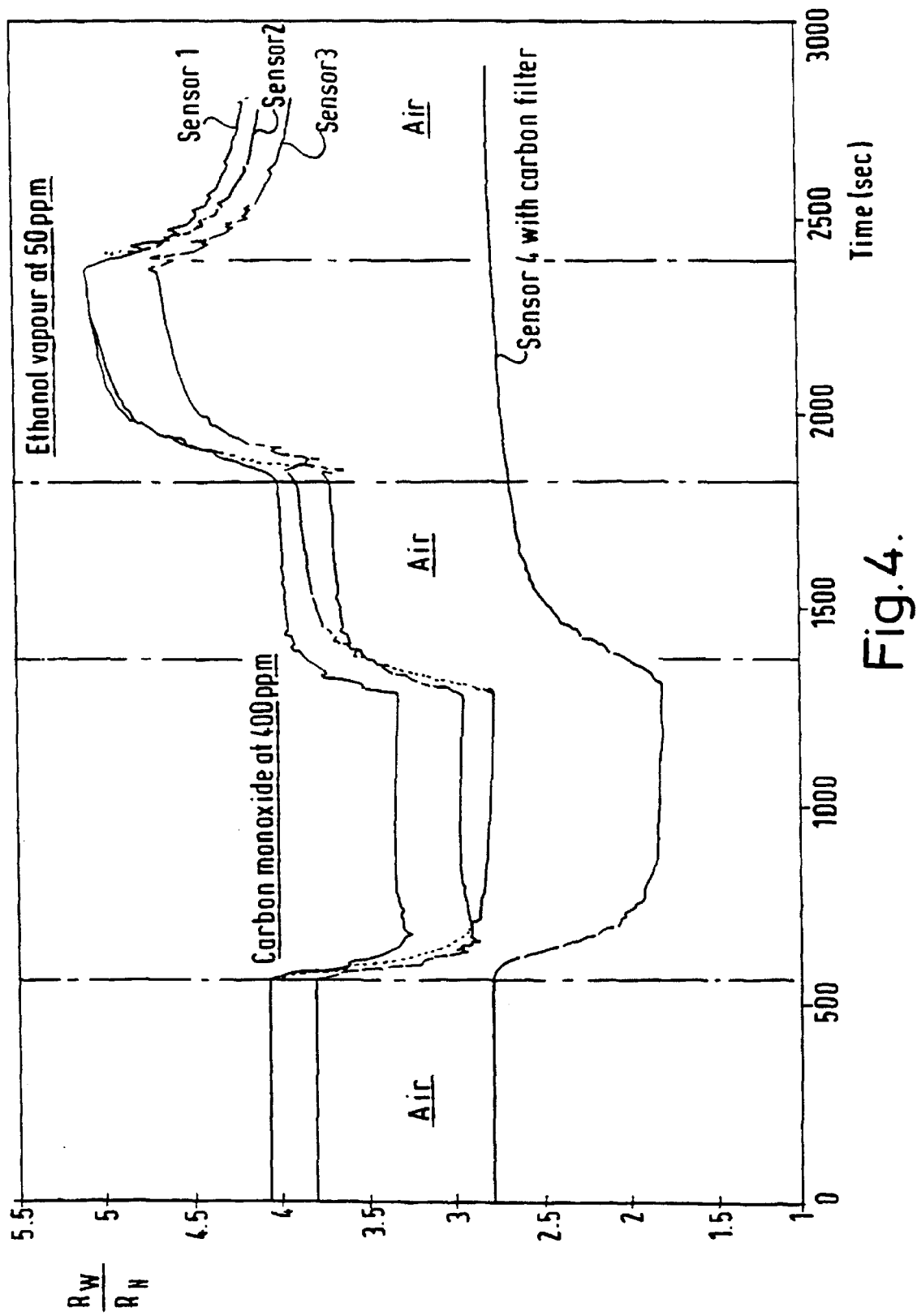
FIG. 4 is a diagram which shows the variation of resistance ratio on exposure of a chromium titanium oxide device according to the invention to carbon monoxide and ethanol at low concentrations in air.

FIG. 4 shows the variation of resistance ratio $R_W/R_N$ for several sensors according to the invention, in response to exposure to carbon monoxide and to ethanol vapour at low concentration in air. The resistance ratio decreased in response to carbon monoxide and increased in response to ethanol.

This effect is believed to arise because carbon monoxide does not have a notable concentration gradient through the thickness of the sensing element, and the sensitivity of the oxide sensing material to gases is greater in the basal region of the sensing element. It appears to the Applicants that the gradation of microstructure is achieved as a consequence of the pressure exerted on the lower sub-layers as further layers are printed on top of them, with this pressure serving somewhat to disaggregate agglomerates and to force finer material into the basal layers of the structure.

EXAMPLE 2

A chromium trioxide-titanium dioxide mixture is prepared by the following steps:
(1) Chromium hydroxide is precipitated from a solution of chromium nitrate (1.8 mole) in water by the addition of ammonium hydroxide, and removed by filtration, being then washed with water but not dried.
(2) Hydrated titanium oxide is precipitated by the addition of titanium iso propoxide (0.2 mole) to pure water, with rapid stirring, and separated by filtration, being then washed with water but not dried.
(3) The powders are mixed and re-suspended in water by stirring in a rotary evaporator flask immersed in an ultrasonic bath. The combined action of the ultrasound and stirring produces a mixed colloidal dispersion of the hydrated oxides. With continued stirring and sonication, the water is removed by vacuum. The resulting powder is removed, dried and filtered to prepare the mixed oxide.

In contrast to the material prepared as in Example 1, material made in this way has been found to have a basic crystallite size of less than about 0.1 μm. Sensors prepared by screen printing of this material, in the same way as in Example 1, have been found to have significantly increased sensitivity to carbon monoxide (R in 400 ppm CO/R in air is about 4.6, in contrast to values of about 3 for the material of Example 1). However, Table 2, below, shows that the ratio $R_W/R_N$ increases, surprisingly, for carbon monoxide as well as for propan-2-ol, if not to the same extent.

The explanation of this phenomenon is that the increased internal surface area results in a sufficient increase in combustion rate, and decrease in diffusivity, to cause a concentration gradient of carbon monoxide to appear.

TABLE 2

Resistance Ratio for Sensors of Example 2

|  | Air | Propan-2-ol (200 ppm) | Carbon monoxide (400 ppm) |
|---|---|---|---|
| $R_W$ $R_N$ | 3.8 | 6.2 | 4.7 |

EXAMPLE 3

A sensing device is prepared by printing the first 20 μm of the thickness in two layers, using material prepared as in Example 2. The next 70 μm of thickness is applied in seven layers, using material prepared as in Example 1. The resulting device is found to have, on the narrow electrode gap, an enhanced sensitivity to CO but not ethanol. As a consequence:

(a) On exposure to ethanol, the signal is no bigger than that in Example 1, and the ratio $R_W/R_N$ increases as in Example 1.
(b) On exposure to carbon monoxide, the signal (using the narrow gap) is increased above that obtained in Example 1, and approaches that obtained in Example 2.
(c) The ratio $R_W/R_N$ is found to decrease on exposure to carbon monoxide, and this decrease is larger than with the sensor material of Example 1. Therefore the device of the present Example has both an improved sensitivity to Co and an improved discrimination between CO and ethanol.

EXAMPLE 4

A sensor comprising a porous layer of tin dioxide is prepared by mixing a commercially available tin dioxide powder (e.g. from the Aldrich Chemical Company) with a screen-printing medium. The sensing element is applied by printing in a succession of layers with intermediate drying, following the general procedures of Example 1. The resulting devices are fired and tested. This has been found to produce a coarse, open microstructure, as for the material of Example 1.

Figure 5:
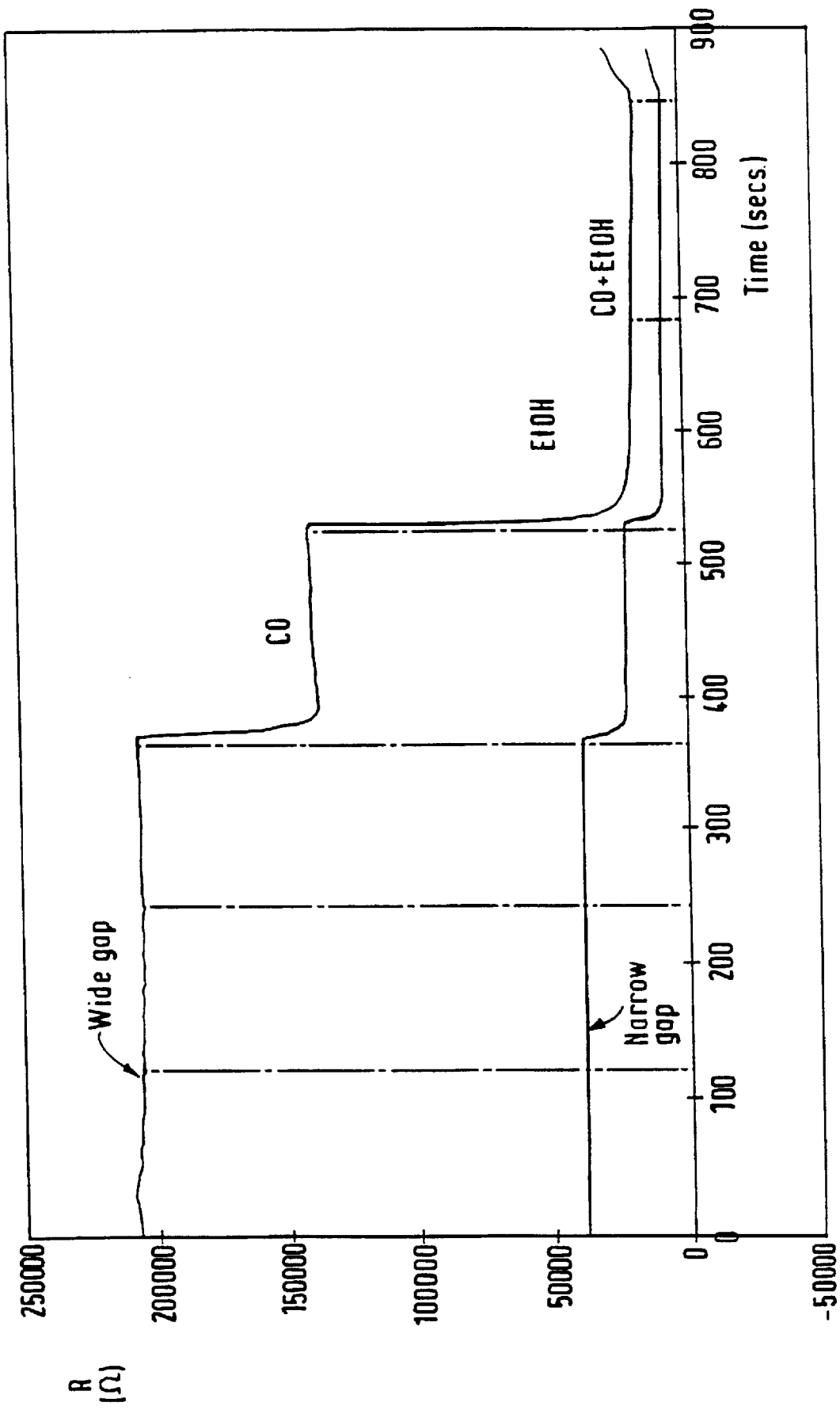
FIG. 5 shows the variation in the resistance itself, of a tin oxide sensor according to the invention having wide and narrow electrode gaps, in response to the presence of low concentrations of carbon monoxide and ethanol in air.
Figure 6:
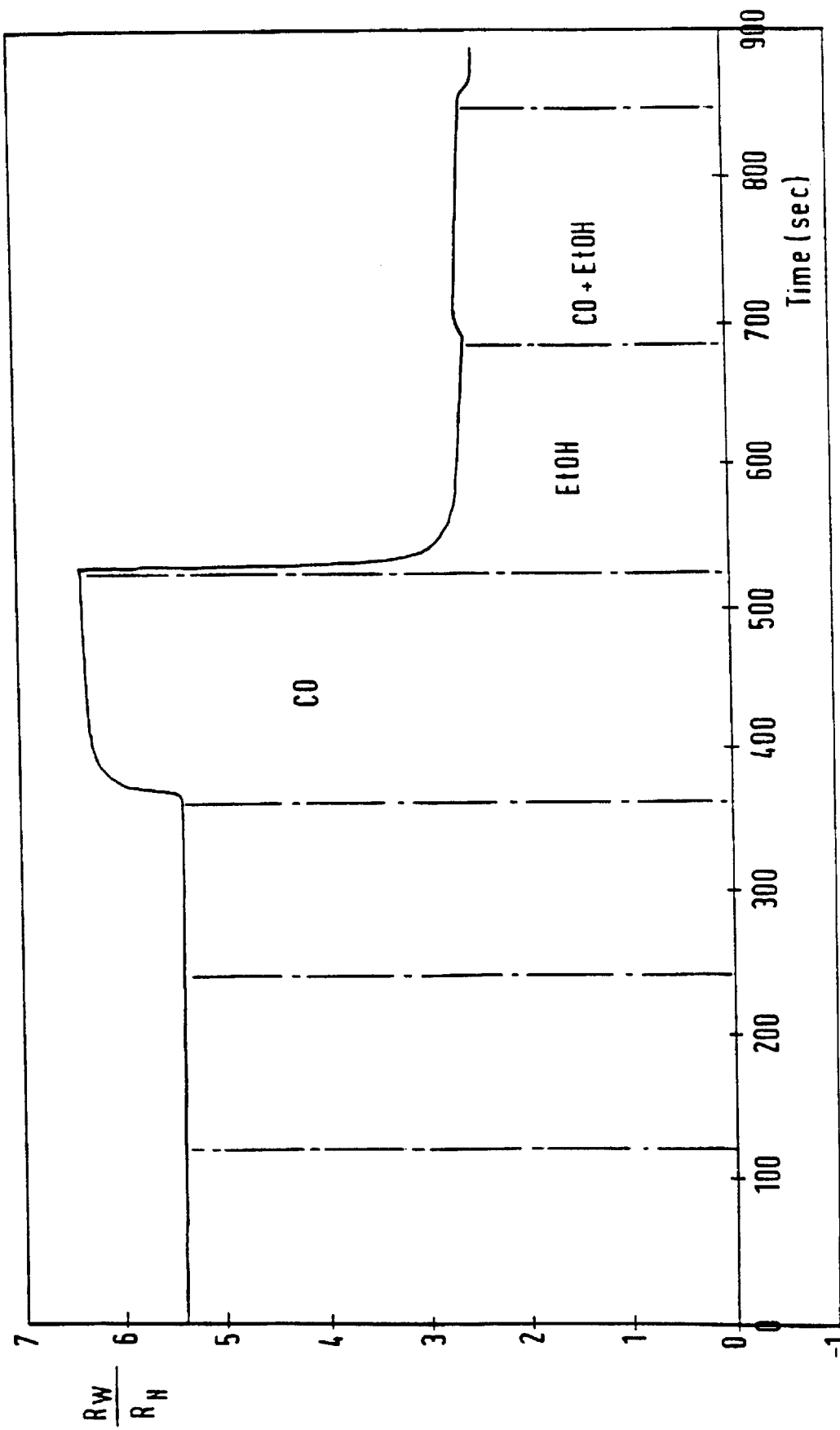
FIG. 6 shows the variation of resistance ratio for a tin oxide sensor on exposure to low concentrations of carbon monoxide and ethanol in air.

FIG. 5 shows that the resistance of these devices has been found to fall on exposure to low concentrations of both carbon monoxide and ethanol in air, reflecting the fact that tin dioxide is an n-type material, in contrast to chromium titanium oxide, which is p-type. FIG. 6 shows that the two gases could again be distinguished from each other by observing the behaviour of the resistance ratio $R_W/R_N$.

The expected behaviour is now a fall in this ratio, corresponding to a larger signal on the wide electrode gap, and this has indeed been found for ethanol. Again surprisingly, the resistance ratio changed in the opposite direction for carbon monoxide, which the Applicants attribute to the gradation of microstructure caused, as mentioned earlier, by the process of printing the devices in successive layers with intermediate drying.

EXAMPLE 5

In this example, it is demonstrated that a multiple-electrode gas sensor can distinguish between a combustible gas and a non-combustible gas.

In this case, by way of non-limiting example only, these gases are acetone and ammonia respectively. The sensor device in this example is modified from one described in the Williams II paper cited above, in that it is 3 mm square and has three pairs of electrodes, with gaps of 20, 40 and 200 $\mu$m. The signals from the small and medium gaps have been found to be virtually identical to each other: therefore only the results from the wide and medium gaps are considered here. The electrodes used in this case were of screen printed, laser-trimmed gold, on an alumina substrate which carried a platinum heater track printed on the obverse side. The gas sensing material was $Cr_{2-x}Ti_xO_{3+y}$, where $0.45 \geq x \geq 0.1$, y being as defined earlier herein.

This oxide was admixed with 25% w/w platinised (5%) alumina powder, and printed to a thickness of 100 $\mu$m.

Experiments have been performed by applying either acetone (0.05–10 Nm$^2$) in air or ammonia (0.8–50 Nm$^{-2}$) in air to this self-diagnostic sensing device, at temperatures between 593° K. and 744° K. The device response, $G=R_{gas}/R_{air})-1$ (as to which, see the Williams I paper), was calculated for each electrode pair.

Figure 7:
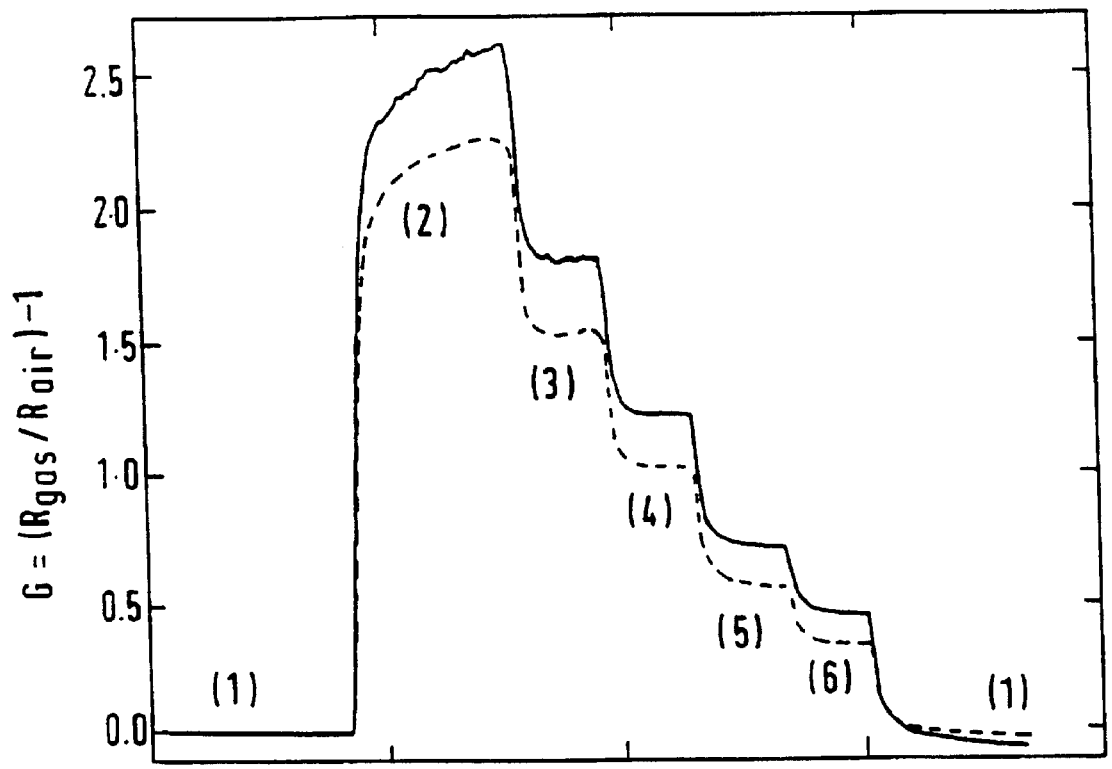
FIG. 7 is a graph of the response against time for a multi-electrode chromium titanate sensor in the presence of acetone.
Figure 9:
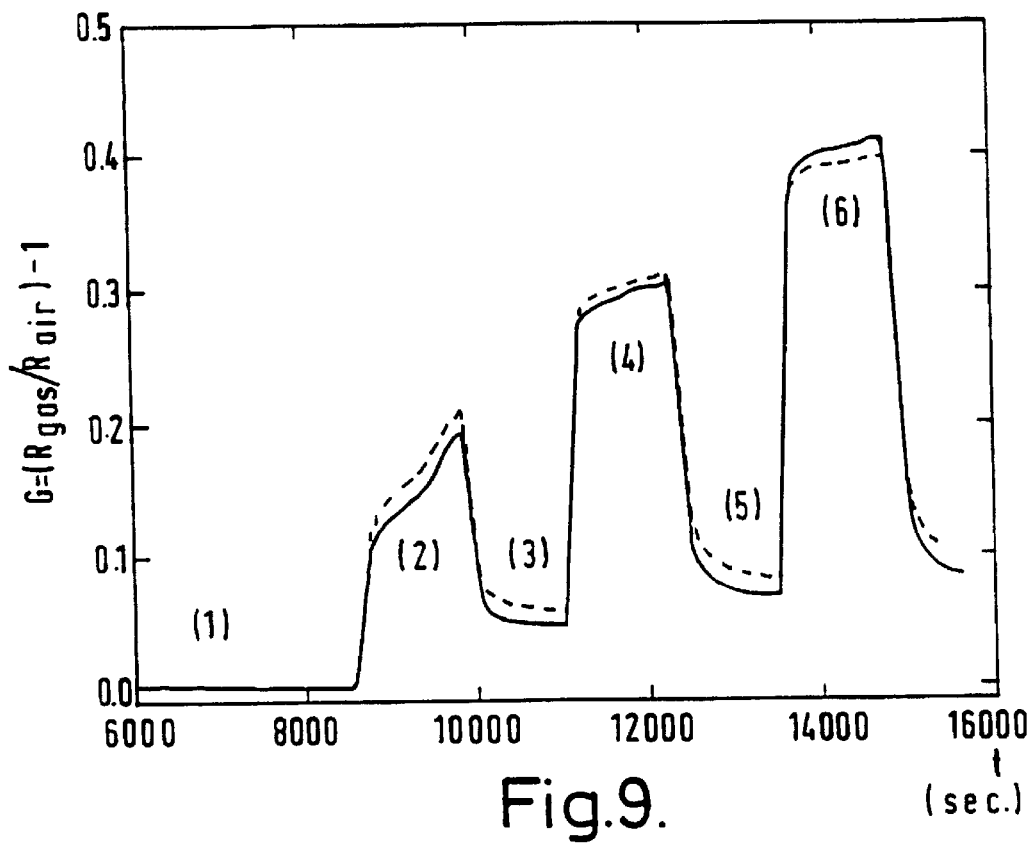
FIG. 9 is a graph similar to FIG. 7 for the same sensor in the presence of ammonia.

Typical behaviour for acetone and ammonia is shown in FIGS. 7 and 9 respectively. FIGS. 7 and 9 show the response G to acetone and ammonia, respectively, as a function of time for the wide (200 $\mu$m) gap, shown as a continuous line, and for the medium (40 $\mu$m) gap shown as a broken line. The readings for both Figures were taken at a temperature of 664° K. for the following acetone or ammonia concentrations (all in Nm$^{-2}$):

|     | FIG. 7 | FIG. 9 |
| --- | --- | --- |
| (1) | 0 | 0 |
| (2) | 10 | 12.5 |
| (3) | 5 | 0.8 |
| (4) | 2.5 | 25 |
| (5) | 0.1 | 0.8 |
| (6) | 0.05 | 50 |

It will be evident from FIGS. 7 and 9 that a concentration gradient exists for acetone, but not for ammonia. Therefore the two gases can be distinguished and simultaneously detected, using, for example, the methods described in the Williams I paper or in the document WO92/21018.

Figure 8:
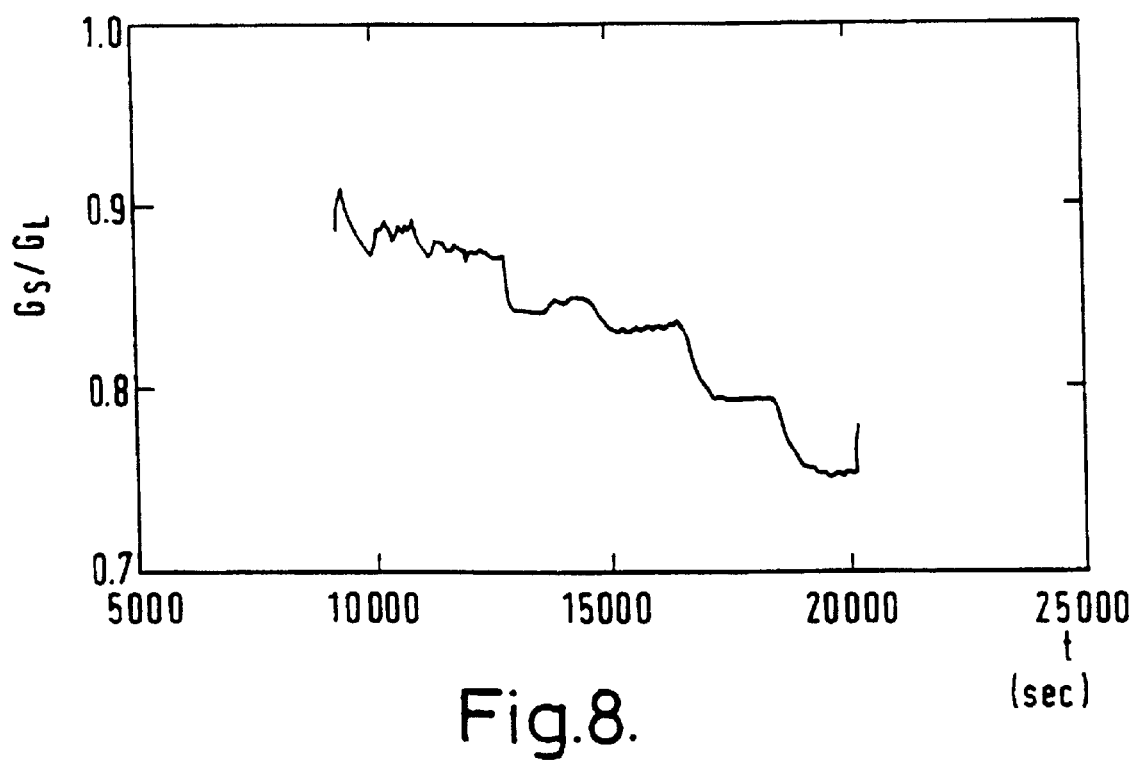
FIG. 8 is a graph showing the variation with time of the ratio of the responses on a wide gap and a narrow gap between electrodes of the sensor, for the same data, and on the same time base, as FIG. 7.

FIG. 8 shows the response of the medium electrode gap relative to that of the wide gap, for the same acetone data. It can be seen that the concentration gradient decreases with increasing gas concentration. In this connection, it should be noted that the Applicants have found that the combustion kinetics are liable to become oxygen limited, a phenomenon with which FIG. 8 is consistent. For simplicity, however, the kinetics are treated as pseudo first order in this case, and a correction is made by extrapolation (see below). The concentration gradient becomes steeper with increasing temperature, as expected.

Using the nomenclature described in Williams I, the response of the device towards acetone will now be analysed in terms of the dimensionless parameters $K_p$, $K_T$ and $\beta$.

As already mentioned, $K_T=kh^2/D$, with k the first order rate constant, h the layer thickness and D the gas diffusivity. The parameter $K_p$ is given by $Kp=A_g c^\beta$, where Ag is the response coefficient. From the data, the value of $\beta$, the order of the response, was found to be 0.6. This unusual value of $\beta$ (values of 1, ½, ¼ etc. are common) is thought to be due to morphological effects on the observed response.

For the planar geometry used here, it was shown in the Williams I paper that the dependence of normalised response on $K_T$ was approximately independent of $K_p$, for $K_p<10$. Given this, the value of $K_T$ could be determined independently of $K_p$, simplifying the analysis and greatly reducing the number of simulations required.

Figure 10:
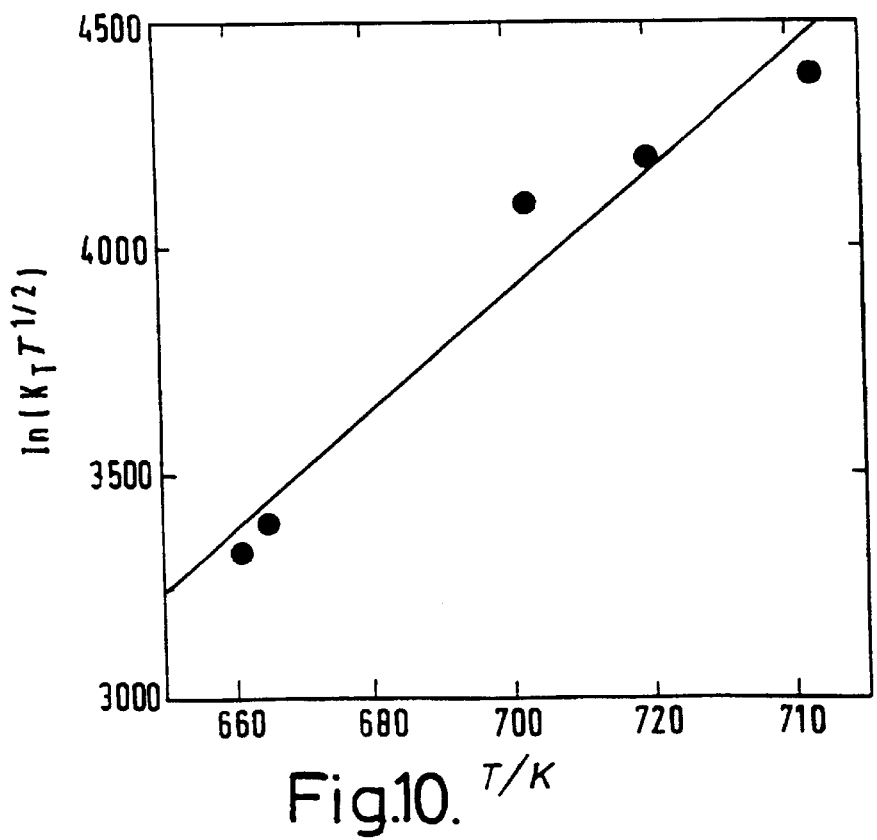
FIG. 10 is a graph showing the temperature dependence of the kinetic parameter $K_T$ for the response of the self-diagnostic sensor to acetone.

Numerical simulation was used to predict the ratio $G_S/G_L$ as a function of the parameter $K_T$ for $\beta=0.6$ and $K_p=1$. This was then used for the determination of the apparent value of $K_T$ for each value of concentration and temperature. A corrected value of $K_T$ (in the absence of oxygen-limited kinetics) at each temperature was then determined by extrapolation of the apparent $K_T$ values to zero acetone concentration, since the kinetics would indeed become first order at low gas concentrations. An Arrhenius dependence of $K_T$ with temperature was observed (see FIG. 10). The value of the parameter k/D was thus found to be $5.7 \times 10^9 e^{-5380/T} T^{1/2}$ cm$^{-2}$. This is several orders of magnitude higher that values determined by the Applicants for uncatalysed materials, as would be expected because of the platinum catalyst admixed into the sensor material.

From the simulated data and calculated values of $K_T$, the temperature dependence of the response coefficient $A_g$ was found to be $12.7 e^{-0.02r}(Nm^2)^{-0.6}$. The computed value of $K_p$ varies from 0.1 to 5.2 over the temperature and concentration range studied, justifying the approximation $K_p<10$.

We claim:

1. In a resistive gas sensor including: a porous gas sensing element comprising an oxide as active gas-sensitive material, said sensing element having a working surface for contact with an atmosphere; and at least three electrodes in electrical contact with said sensing element, for receiving signals from different regions of said sensing element, the improvement wherein said sensing element has a basal layer in electrical contact with said at least three electrodes, said basal layer being overlaid with a plurality of sub-layers, each sub-layer having a different microstructure from the other sub-layers or -layer whereby the microstructure from the basal layer through the plurality of sub-layers changes in coarseness from said basal layer to said working surface.

2. A sensor according to claim 1, wherein said electrodes comprise a first electrode, a common second electrode defining a narrow gap between said first and second electrodes, and a third electrode defining a wide gap between said second and third electrodes, whereby output signals from said first electrode represent electrical resistance in a basal region of the sensing element close to said electrodes, and output signals from said third electrode represent resistance across the whole thickness of said sensing element defined between said electrodes and said working surface.

3. A sensor according to claim 2, wherein each of said first and second electrodes includes a set of strip portions, interleaved with those of the other electrodes to define the narrow gap as a serpentine gap.

4. A sensor according to claim 1, wherein the active sensing material is chromium titanium oxide, with an impurity content comprising $Cr_2O_3$ in the inclusive range 0–30 mol % and/or $TiO_2$.

5. A sensor according to claim 4, wherein the active material is $Cr_{2-x}Ti_xO_{3+y}$, where $0.45 \geq x \geq 0.1$, and y is a variable dependent on temperature and oxygen partial pressure.

6. A sensor according to claim 1, wherein said sensing element has an impurity content comprising one or more elements in the inclusive range 0–1 atom %.

7. A sensor according to claim 1, wherein said sensing element includes up to 30% by weight of catalytically active material.

8. A sensor according to claim 7, wherein said catalytically active material is dispersed on the surface of said active material.

9. A sensor according to claim 8 wherein at least one said sub-layer includes said catalytically active material mixed with the active material of that sub-layer.

10. A sensor according to claim 7, wherein said catalytically active material is mixed with said active material.

11. A method of detecting a target gas in a mixture of gases, using a resistive gas sensor having at least three electrodes to produce electrical resistance signals, the method including the steps of processing said signals to obtain information about the target gas and/or the mixture, wherein said resistive gas sensor is a sensor according to claim 1.

12. A method according to claim 11 in which the mixture includes a reactive first gas and a less reactive second gas, wherein the sensor used has a sensing element the active sensing material of which displays a concentration gradient across the sensing element in response to the first gas, but substantially none in response to the second gas.

13. A method according to claim 12 in which the second gas is carbon monoxide, and wherein said sensor is a sensor according to claim 4.

14. A method of manufacturing a resistive gas sensor wherein said sensor includes a porous gas sensing element comprising an oxide as active gas-sensitive material, said sensing element having: a working surface for contact with an atmosphere, at least three electrodes for receiving electrical signals from different regions of said sensing element, a basal layer in electrical contact with said at least three electrodes, said basal layer being overlaid with a plurality of sub-layers, each sub-layer having a different microstructure from the other sub-layers or -layer whereby said microstructure from said basal layer through the plurality of sub-layers increases in coarseness from said basal layer to said working surface, said method comprising the steps of screen printing each sub-layer over the electrodes or a selected surface area of the electrodes, or over the last preceding sub-layer as the case may be, and dying each sub-layer before application of any further sub-layer.

* * * * *